United States Patent [19]

Demarne

[11] 4,252,825

[45] Feb. 24, 1981

[54] COMPOSITIONS FOR TREATMENT OF CARDIOVASCULAR CONDITIONS ASSOCIATED WITH OVERPRODUCTION OF CATECHOLAMINES

[75] Inventor: Henri Demarne, Montpellier, France

[73] Assignee: C. M. Industries, Paris, France

[21] Appl. No.: 1,314

[22] Filed: Jan. 5, 1979

Related U.S. Application Data

[60] Division of Ser. No. 781,490, Mar. 25, 1977, which is a continuation of Ser. No. 590,727, Jun. 26, 1975, abandoned.

[30] Foreign Application Priority Data

Jun. 28, 1974 [GB] United Kingdom ............... 28925/74

[51] Int. Cl.³ ............................................ A61K 31/135
[52] U.S. Cl. .................................. 424/330; 424/331; 564/351

[58] Field of Search ............................... 424/330, 331; 260/570.7

[56] References Cited

U.S. PATENT DOCUMENTS

| | | | |
|---|---|---|---|
| 3,501,769 | 3/1970 | Crowther | 260/570.7 |
| 3,875,149 | 4/1975 | Wooldridge | 260/570.7 |

FOREIGN PATENT DOCUMENTS 1084793  9/1967  United Kingdom ................. 260/570.7

*Primary Examiner*—Anna P. Fagelson

[57] ABSTRACT

Compositions having therapeutic value in the treatment of cardiovascular conditions associated with the overproduction of catecholamines include as the active ingredient 5-fluoro-2-(2-hydroxy-3-tertiary butyl-aminopropoxy) butyrophenone-, its optical isomers and non-toxic acid addition salts.

6 Claims, No Drawings

COMPOSITIONS FOR TREATMENT OF CARDIOVASCULAR CONDITIONS ASSOCIATED WITH OVERPRODUCTION OF CATECHOLAMINES

This is a division of application Ser. No. 781,490 filed Mar. 25, 1977, now abandoned, which is a continuation of application Ser. No. 590,727, filed June 26, 1975, now abandoned.

This invention relates to aromatic ketones which have cardiovascular activity and more especially to derivatives of 3-amino-2-hydroxy-1-phenoxypropane which have an acyl group and a halogen atom as substituents in the benzene ring.

The invention also relates to a method of preparing the ketones of the invention and to pharmaceutical compositions containing the same. It further relates to new intermediate products which are used in the synthesis of the products having the general formula I.

According to the present invention there are provided:

(a) the racemates and optical isomers of the substituted 3-amino-2-hydroxy-1-phenoxypropanes having the general formula:

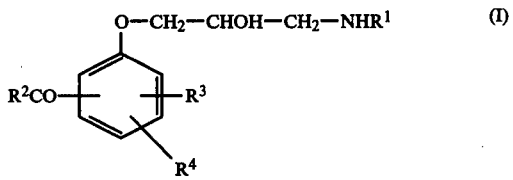

in which $R^1$ and $R^2$ are the same or different and each represents an alkyl group having 1 to 4 carbon atoms, $R^3$ is a hydrogen atom or an alkyl group having 1 to 4 carbon atoms, and $R^4$ is a halogen atom and in particular a fluorine, chlorine or bromine atom, with the proviso that $R^3$ is other than a hydrogen atom when, simultaneously, $R^1$ is isopropyl, $R^2CO$ is acetyl or propionyl in an ortho position with respect to the ether function, and $R^4$ is a chlorine atom in the para position with respect to the ether function, (b) the addition salts which they form with acids.

The two products which are excluded by the above proviso, namely 5-chloro-2-(2-hydroxy-3-isopropylaminopropoxy)propiophenone and 5-chloro-2-(2-hydroxy-3-isopropylaminopropoxy)acetophenone are stated in French Special Medicine Pat. No. 7616M to be intermediates in the synthesis of imines.

Surprisingly, it has just been found that the compounds having the general formula I, and, in general, the compounds having the general formula Ia:

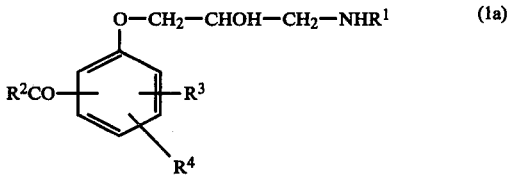

in which $R^1$ is an alkyl group having 1 to 4 carbon atoms, $R^2$ is an alkyl group having 1 to 4 carbon atoms, $R^3$ is a hydrogen atom or an alkyl group having 1 to 4 carbon atoms, and $R^4$ is a halogen atom, are cardiovascular agents of the β-blocking type the effect of which is usually greater than, or at least equal to, that of propranolol[3-isopropylamino-1-(α-naphthoxy)-2-propanol], which is a well-known reference compound, and that of the phenoxy homologues of propranolol which are described in French Special Medicine Pat. No. 4061 and the corresponding French Pat. No. 1,394,771.

The alkyl groups $R^1$, $R^2$ and $R^3$ may be straight or branched chain alkyl groups. By halogen atom is to be particularly understood an atom of fluorine, chlorine or bromine. The preferred values for the groups $R^1$, $R^2$, $R^3$ and $R^4$ according to the invention are $R^1$ is $CH(CH_3)_2$ or $C(CH_3)_3$, $R^2$ is methyl, ethyl or propyl, $R^3$ is hydrogen or methyl and $R^4$ is fluorine, chlorine or bromine.

The compounds having the general formula I may be prepared (a) by a known method involving the application of conventional reaction mechanisms, or (b) by an original method which includes the production of an intermediate product, viz: 8-aza-4,9-dioxa-2,3-benzo[4.2.1]bicyclooctane having the general formula 4. Methods A and B as recommended in accordance with the invention are described below.

METHOD A

The compounds having the general formula I may be synthesised in two stages from a hydroxyacylophenone having the general formula II, the stages being:

(a) the ethers III are obtained by the action of 1-halo-2,3-epoxypropane on a hydroxyacylophenone having the general formula II in the presence of an alkaline agent such as caustic soda or caustic potash dissolved in a solvent such as water, ethanol or a polyglycol such as diethylene glycol or an ether of a polyol such as ethylene glycol monoethyl ether; and (b) by reacting a primary alkylamine having the general formula $R_1NH_2$ with the ethers III in solution in a solvent such as absolute ethanol, the compounds I are obtained. These may if desired be converted into their salts by treatment with a mineral or an organic acid.

The haloepoxide used in stage (a) may in particular be a fluorinated, chlorinated or brominated derivative. In the examples given below the epoxide used was 1-chloro-2,3-epoxypropane.

The reaction constituting stage (a) is conveniently brought about at a temperature between 78° C. (the reflux temperature of ethanol) and about 130° C., for from 15 minutes to 5 hours.

The reaction constituting stage (b) takes place in the presence of an excess of an amine having the general formula $R_1NH_2$ (a 20% stoichiometric excess) for 2 hours at the reflux temperature of the reaction medium.

This method of synthesis of the compounds having the general formula I may be illustrated diagrammatically as follows:

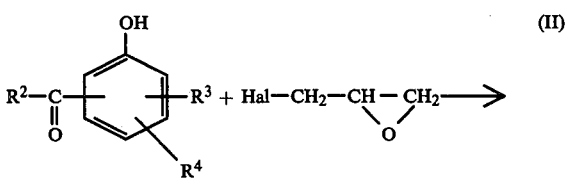

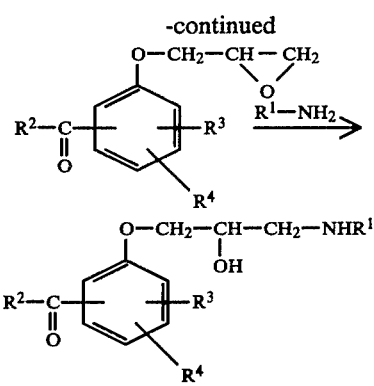

in which $R^1$, $R^2$, $R^3$ and $R^4$ are as defined above.

The hydroxyketones II are known substances which are obtained by means of the Fries reaction from the corresponding esters of halophenols. In practice, the ethers III are frequently accompanied by a variable quantity of the corresponding chlorohydrin IIIa:

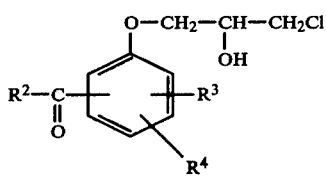

It is unnecessary to separate the constituents of the mixture since both constituents, when treated with an amine of the formula $R^1NH_2$, give the desired compounds I.

Method A may be used for the synthesis of compounds Ia.

METHOD B

This is an original method for preparing a compound, 3-(2-acylphenoxy)-1-alkylamino-2-propanol, having the general formula

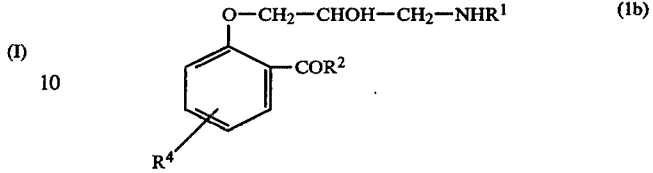

in which $R^1$, $R^2$ and $R^4$ are as defined above, which method comprises five stages, viz:

(a) reacting a substituted salicylic aldehyde having the general formula 1 with a 1-alkylamino-2-hydroxy-3-chloropropane having the general formula 2 in an anhydrous aprotic solvent such as benzene, in the presence of a dehydrating catalyst, such as para-toluenesulphonic acid;

(b) the resulting 3-alkyl-5-chloromethyl-2-(2-hydroxyphenyl)-oxazolidine having the general formula 3 is subjected to ring-closure in a dipolar aprotic solvent (such as dimethylformamide or tetrahydrofuran) using a basic agent, such as sodium hydride.

(c) the 8-aza-4,9-dioxa-2,3-benzo-[4.2.1]bicyclooctane having the general formula 4 thus obtained is subjected to acid hydrolysis for approximately 8 hours, using, for example, 1 N hydrochloric acid;

(d) the 2-(3-alkylamino-2-hydroxypropoxy)benzaldehyde having the general formula 5 thus obtained is reduced by means of an organo magnesium compound of the general formula $R^2MgBr$; and (e) the resulting substituted benzyl alcohol having the general formula 6 is oxidised using a stoichiometric amount of chromic acid at a temperature of 5° to 10° C. in the presence of 12 N sulphuric acid.

This method may be illustrated diagrammatically as follows:

DIAGRAM B

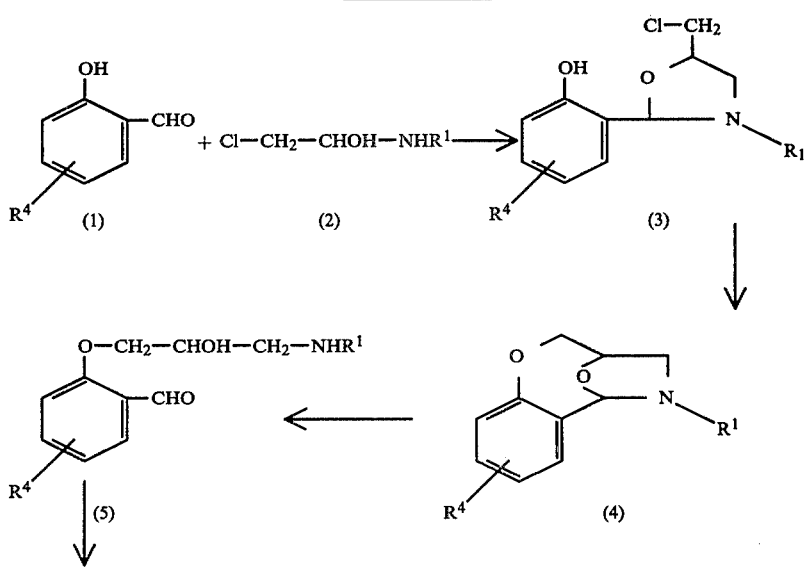

DIAGRAM B

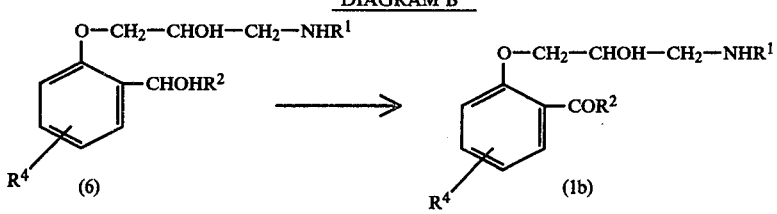

Method B is applicable to the production of the compounds having the general formula 1b in which $R^4$ is an alkyl group having 1 to 4 carbon atoms, an alkoxy group having 1 to 4 carbon atoms, or a hydrogen atom.

The addition salts with acids of the compounds having the general formulae I and Ia are obtained by reacting the corresponding free base with a mineral or organic acid using a conventional method. Among the acids whch may be used for this purpose may be mentioned hydrochloric, sulphuric, phosphoric, formic, acetic, propionic, benzoic, cinnamic, oxalic, fumaric, maleic, malic, lactic, citric, tartaric, ascorbic, salicylic, acetylsalicylic, aspartic, glutamic, methanesulphonic, p-toluenesulphonic and malonic acids.

The optical isomers present in the products having the general formulae I and Ia may, if desired, be separated using a known method by treating a racemic base with an optically active acid such as one of the d- or l-tartaric acids, the d- or l-dibenzoyl tartaric acids or the d- or l-di-p-toluoyl tartaric acids.

The present invention also provides therapeutic compositions which are particularly useful in the treatment of hypertension, heart-beat disorders and conditions of the cardio-vascular system, which compositions contain, together with a physiologically acceptable excipient, at least one racemate or optical isomer having the general formula 1a or a non-toxic acid addition salt of such racemate or optical isomer.

A number of compounds according to the invention are listed in the appended table I, the position of the various substituents on the benzene ring being defined with respect to the ether function which is arbitrarily assumed to be in the 1 position. (In the examples of preparation the standard convention is adopted in accordance with which the acyl group $R^2CO$ is in the 1-position. Some examples of preparation are given below to illustrate the invention but they are in no way limiting. Preparations A1 to A3 relate to method A, preparation B illustrates the production of a product using method B, and finally, preparation C deals with the separation of the optical isomers.

PREPARATION A1

5-Fluoro-2-(2-hydroxy-3-isopropylaminopropoxy) propiophenone (Code No. CM 6719)—Example 2 in Table 1

(a) 2-(2,3-epoxypropoxy)-5-fluoropropiophenone 15 gms. of 5-fluoro-2-hydroxypropiophonone is dissolved in a mixture of 125 ml of ethylene glycol and 125 ml of 1-chloro-2,3-epoxypropane. The mixture is heated to 80° C. and 4.5 g of caustic soda pellets is added all at once. The temperature of the mixture is raised to 130° C. and this temperature is maintained for 15 minutes. After cooling, the mixture is poured into water and the organic phase is extracted with diethyl ether. The ether solution is separated, washed with water, dried over anhydrous sodium sulphate and then evaporated to dryness. The residual oil crystallises on cooling. Yield=14 g. The product is used as it is obtained for the succeeding preparation.

(b) CM 6719

The product obtained as described above (14 g) is dissolved in 50 ml of ethanol and then 3.7 g of isopropylamine (20% excess) is added and the mixture is refluxed for 2 hours. After the solvent has been evaporated under reduced pressure (15 mm of mercury) the residue is dissolved in dilute acetic acid. The aqueous phase is extracted with diethyl ether and then rendered alkaline with sodium carbonate. The organic product which separates out is extracted with diethyl ether and the organic phase is separated, washed with water and dried over anhydrous sodium sulphate. It is then evaporated to dryness and the residue crystallises on cooling. It is recrystallised from diisopropyl ether. Yield=12.8 g. Melting point=114°-115° C.

PREPARATION A2

5-Chloro-2-(2-hydroxy-3-tertiarybutylaminopropoxy)-propiophenone (Code No. CM 6785)—Example 4 in Table 1

(a) 5-chloro-2-(2,3-epoxypropoxy)propiophenone.

15 g of 5-chloro-2-hydroxypropiophenone is dissolved in a mixture of 75 ml of water and 20 ml of absolute ethanol and then 3.5 g of caustic soda pellets and 9.2 g of 1-chloro-2,3-epoxypropane are added. The mixture is heated upon a boiling water bath for 5 hours and then, after cooling, extracted with diethyl ether. The ethereal phase is separated, washed with water, dried over anhydrous sodium sulphate and the solvent evaporated to dryness. The residual oil is distilled at very low pressure. Yield=7.6 g. Boiling point=134°-138° C./0.3 mm.

(b) CM 6785

3.8 g of the oil obtained as described above is dissolved in 20 ml of absolute ethanol and 1.4 g of tertiarybutylamine is added. The mixture is refluxed for 2 hours. The solvent is evaporated under reduced pressure and the residue dissolved in dilute acetic acid. The aqueous phase is washed with diethyl ether and then rendered alkaline with potassium carbonate. The oil which separates out is extracted with diethyl ether and the organic phase is separated, then washed with water, dried over anhydrous sodium sulphate and the solvent evaporated. The residue crystallises on cooling and is recrystallised from a small volume of methanol. Yield=3.6 g. Melting point=98°-99° C.

PREPARATION A3

Acid fumarate of 5-bromo-2-(2-hydroxy-3-isopropylaminopropoxy)-propiophenone (Code No. CM 6712)—Example 3 in Table 1

The procedure adopted in Preparation A1 is followed except that the 5-fluoro-2-hydroxypropiophenone is replaced by 5-bromo-2-hydroxypropiophenone. 3.4 g. of free base is obtained in this way from 5.5 g of the latter substance. This base, together with 1.2 g of fumaric acid, is dissolved in 15 ml of boiling ethanol and is left to crystallise on cooling. The crystals which separate are filtered and the acid fumarate is recrystallised from absolute ethanol. Yield=3.5 g. Melting point=165°–166° C.

PREPARATION B

5-Fluoro-2-(2-hydroxy-3-tertiarybutylaminopropoxy) butyrophenone (Code No. CM 6805)—Example 7 in Table 1

Alternative name for this product: 1-(2-butyryl-4-fluorophenoxy)-2-hydroxy-3-tertiarybutylaminopropane.

(a) 5-chloromethyl-3-tertiarybutyl-2-(2-hydroxy-5-fluorophenyl)oxazolidine

5-Fluorosalicylaldehyde (1.4 g, 0.01 mole) is dissolved in anhydrous benzene (20 ml) in the presence of a crystal of paratoluenesulphonic acid in a Dean-Stark apparatus. 1-Chloro-2-hydroxy-3-tertiarybutylaminopropane (2.08 g, approximately 1 equivalent, purity 75%) is then added within a period of 10 hours in portions of 250 mg at a time at the reflux temperature of benzene and the mixture is allowed to stand overnight. An insoluble substance is precipitated on addition of ether after which the solution is filtered, concentrated and distilled. A fraction is obtained having a boiling point of 118°–123° C./$10^{-3}$ mm of mercury. A mixture of 1.03 g (yield 43%) of isomeric oxazolidines is obtained which solidifies. This is crystallised once from hexane. Melting point 75°–78° C.

Analysis $C_{14}H_{19}FClNO_2$ (molecular weight: 287.76)
Calculated: C 58.44%, H 6.65%, N 4.86%, Cl 12.32%
Found: C 58.64%, H 6.78%, N 4.72%
NMR (CHCl$_3$): Peaks at $\delta$=5.58 and 5.67 ppm (1H)
$\delta$=1.1 ppm (9H)

(b) 8-aza-4,9-dioxa-11-fluoro-8-tertiarybutyl-2,3-benzobicyclo[4.2.1]octane

The product of the previous stage (620 mg) is dissolved in anhydrous dimethyl formamide (10 ml) and two quantities each of 300 mg of 50% sodium hydride is added within 2 hours. The mixture is then left for 24 hours at 25° C. while being stirred mechanically and is then heated for 2 minutes on a water bath (80°–90° C.). The mixture is poured into water, the product extracted with ether, the ethereal extract dried over anhydrous sodium sulphate and the organic phase then concentrated and filtered through a short column of activated alumina. A mixture of light petroleum and diethyl ether (75:25) is used to elute 186 mg of pure product from the column. Melting point 85°–86° C. (after recrystallisation from diisopropyl ether).

(c) 1-(2-formyl-4-fluorophenoxy)-2-hydroxy-3-tertiarybutylaminopropane

The compound obtained as described above (50 mg) is dissolved in a solution of 1 N hydrochloric acid (0.5 ml). The mixture is then heated on a water bath (80°–90° C.) for several hours. After complete hydrolysis, which requires approximately 8 hours, the mixture is poured into an excess of water which has been basified, the solid base thus formed is extracted with ether, dried and recrystallised from diisopropyl ether. Melting point: 103°–105° C.

Analysis: Infrared spectrum (CH$_2$Cl$_2$): 1681 cm$^{-1}$.

(d) 1-[2-(1-hydroxybutyl)-4-fluorophenoxy]-2-hydroxy-3-tertiarybutylaminopropane To a solution of propylmagnesium bromide prepared from 195 mg ($8.1 \times 10^{-3}$ mole) of magnesium, 1.0 g ($8.1 \times 10^{-3}$ mole) of bromopropane and a crystal of iodine in 10 ml of anhydrous diethyl ether under nitrogen is added a solution of the previously prepared aldehyde (197 mg, $0.73 \times 10^{-3}$ mole) in 4 ml of an ether/tetrahydrofuran mixture (1:3 by volume) and the mixture is heated to reflux for 70 minutes. The mixture is poured into water, extracted with diethyl ether, dried over anhydrous sodium sulphate and 208 mg of an oil which is homogeneous, as shown by thin-layer chromatography, is isolated. The neutral fumarate is formed in acetone from an equivalent (77 mg) of fumaric acid and is recrystallised from a mixture of methanol and acetone. 52 mg of neutral fumarate is obtained. Melting point=222°–224° C.

(e) CM 6805

The previously prepared base (200 mg, $0.66 \times 10^{-3}$ mole) is dissolved in purified acetone (8 ml). A drop of sulphuric acid solution (prepared from 35 ml of concentrated sulphuric acid and 65 ml of water) is added and the mixture heated on a water bath for 1 minute. When the solution has cooled to 5° to 10° C. a solution of chromic acid (66 mg, 1 equivalent) dissolved in 2 ml of the same acid solution is quickly added and the resulting mixture is stirred while cold. The mixture is then poured into a saturated solution of sodium carbonate, the acetone is evaporated under reduced pressure on a water bath, and the organic phase is extracted with diethyl ether. After drying and evaporating the solvent an oil is obtained (172 mg) all of which solidifies. Recrystallisation is carried out from di-isopropyl ether. 122 mg of CM 6805 is obtained (yield 61%). Melting point 88°–89° C.

PREPARATION C

Separation of the enantiomorphs of CM 6805

(1) 15.6 g of the CM 6805 racemate (dl) ($5 \times 10^{-2}$ mole) and 25 g of (+) O,O'-ditoluoyl tartaric acid are dissolved in 200 ml of boiling anhydrous ethanol. The reaction product is allowed to crystallise by very slowly cooling (24 hours). The salt which separates is filtered and is twice recrystallised from 60 ml of anhydrous ethanol and the mother liquors from the two crystallisations are kept. 7.3 g of a salt are obtained, which salt is the (+)O,O'-ditoluoyl tartrate of (+)1-(2-butyryl-4-fluorophenoxy)-2-hydroxy-3-tertiarybutylaminopropane. Melting point=138° to 140° C. (Kofler).

This salt is dissolved in 50 ml of water, the pH is made alkaline by the addition of 10% caustic soda and the liberated base formed is extracted with methylene chloride. The organic phase is decanted, dried and evaporated to dryness. The crystalline residue is recrystallised from hexane; it is the d isomer of CM 6805 which is obtained (2.8 g). Melting point=60° C. (Kofler). $\alpha_D$=+9.5° (1.4% solution is chloroform; $\lambda$=589,592 nm of sodium).

This isomer has been coded CM 7009.

(2) By evaporating the mother liquors obtained at the time when the above salt of (+)O,O'-ditoluoyltartaric acid was crystallised a salt of CM 6805 which is enriched in the laevorotatory isomer is obtained.

This salt is dissolved in water, made alkaline with 10% caustic soda and the product extracted with methylene chloride. The base obtained is dissolved in 120 ml of anhydrous ethanol which has dissolved therein 15 g of (−)O,O'-ditoluoyl tartaric acid. The solution is allowed to crystallise slowly (over 24 hours) and the salt which separates is filtered. The salt is recrystallised twice using 60 ml of absolute ethanol each time.

7.8 g of the salt is obtained. The salt is the (−)O,O'-ditoluoyl tartrate of (−)1-(2-butyryl-4-fluorophenoxy)-2-hydroxy-3-tertiarybutylaminopropane. Melting point=138° to 140° C. (Kofler).

This salt is dissolved in 50 ml of water and the solution obtained is made alkaline with 10% caustic soda. The base formed is extracted with methylene chloride, dried and the organic solution obtained is evaporated to dryness.

The laevorotatory base crystallises and is recrystallised from hexane. 3.2 g of the laevorotatory isomer (L) of CM 6805 is obtained. Melting point=60° C. (Kofler). $\alpha_D = -9.64°$ (1.4% solution in chloroform, $\lambda = 589.592$ nm for sodium).

This isomer has been coded CM 7010.

Pharmacological tests which have been carried out have shown that among the compounds set out in table I below seven are of particular interest from the point of view of their cardiovascular activity, namely the products of examples 2 (CM 6719), 4 (CM 6785), 6 (CM 6804), 7 (CM 6805), 8 (CM 6826), 10 (CM 6831), and 12 (CM 6833) in that table, the best being CM 6805.

Below are summarised the test procedures adopted in the pharmacodynamic tests to which the seven most interesting products were subjected.

I—Evaluation of adrenolytic effect in the dog

The animal was anaesthetised using sodium pentobarbital which was administered intravenously in amounts of 25 to 30 mg/kg bodyweight. The animal was intubated and allowed to breathe naturally. A canula was inserted in a saphenous vein so as to allow the test substances to be injected.

Surface electrocardiograms were taken at two points (D1 and D2).

A catheter was implanted in a peripheral artery (usual a humeral artery) and was connected to a Statham P 23 Db pressure cell.

Any possible effect the products might have in counteracting the β-stimulating effect of isoprenaline was tested using the following procedure.

First, the dose of isoprenaline which caused an increase of at least 60% in the pulse rate (in general 0.5 to 1 microgram per kilogram bodyweight) was determined. Also measured were the hypotensive changes caused by the same doses of isoprenaline.

The substance under test was then injected intravenously in increasing doses. After each of these injections a fresh dose of isoprenaline determined as described above was also injected. The dose of the substance under test is observed at which a reduction of at least 60% in the pulse-rate accelerating and hypotensive effects of the isoprenaline occurs.

The dosages of the active substances which meet these requirements appear in column A of the appended table II and the percentage reductions in column B (FC in the case of pulse-rate and AP in the case of blood pressure).

The test was repeated over 30 minutes. The time taken by the counteracting effect to fall below 60% is noted. This time is reported in column C.

II—Haemodynamic tests

The haemodynamic consequences of the intravenous injection of a β-blocking dose were tested for the seven products of interest. The following parameters were checked:

Rate of heart-beat (see column D in table II)
Peripheral arterial pressure (see column E)
Pressure in the left ventricle (see column F)
Pressure in the right ventricle (see column G)
Contractility index $(dp)_P - 1/dt)$. Derived from the isovolumetric phase of the left ventricle (see column H)
Cardiac output in milliliters per minute (see column I)
Systolic volume. Cardiac output divided by rate of heart-beat (see column J)
Total peripheral resistance (see column K)
Maximum ventricular frequency (see column L)
The following notation has been employed
= whenever the parameter does not alter.
↑ if there is an increase in the parameter.
↓ if there is a reduction in the parameter.

III—Effect on cardiac conduction

Cardiac conduction was determined:
(1) from the maximum sustained ventricular frequency (column L);
(2) by taking a Hisian electrocardiogram, see Scherlag, Damato Circulation, vol. 39, pages 13 to 18 (1969). The results appear in column M(AH) in the case of supra-Hisian conduction and in column M(HV) in the case of infra-Hisian conduction.

IV—Electrophysiological tests in vivo

These tests were carried out using micro-electrodes.
The effects on the fast conductance of sodium gNa are given in column N of table II.
Changes in the duration of activating potentials in the Purkinje tissue and in the ventricular myocardial tissue are given in columns O and P of table II respectively.

V—Local anaesthetic effect

This was determined by the method of Regnier (Compte-Rendus Acad. Sciences, vol. 177, pages 558–560, 1923).

This test mainly investigates surface anaesthesia.

If procaine is assigned the value 1 and propanolol the value 20, the products described can be classified as follows:

CM 6719=0
CM 6804=0
CM 6831=0
CM 6826=0.15
CM 6833=0.15
CM 6805=0.2
CM 6785=1

From the results given in table II it appears firstly that the seven products are superior to the other products in the group of derivatives of 3-amino-2-hydroxy-1-phenoxypropane and secondly that they exhibit a certain degree of uniformity from the point of view of their pharmacological activity.

The products of the invention are generally of low toxicity.

They may be used for the following therepeutic applications:

(a) Treating pathological conditions associated with the over production of catecholamines, i.e. tachycardia, palpitations, estrasystoles and hyper-tension;

(b) Treatment at the source of anginal conditions; the after-effects of strokes, and disorders of the auricular and ventricular rhythm; and (c) Treatment at the source of hypertensive conditions.

The active substances may be used in various preparations suitable for oral administration, such as tablets containing 5 to 100 mg of active substances, for rectal administration, such as suppositories containing 5 to 100 mg of active substance, and as injectable preparations containing 5 to 25 mg of active substance.

As a rule the dosage will be one to two 25 mg tablets per day but, in exceptional cases and under medical supervision, this figure may be considerably exceeded. Some examples of medicinal preparations are given below:

| (a) Tablets | | (b) Suppositories | |
|---|---|---|---|
| CM 6804 | 25 mg | CM 6805 | 25 mg |
| Microcrystalline | | Suppocire (an injectable | |
| cellulose | 60 mg | mixture of esters of naturally fatty acids) and | |
| Lactose | 276 mg | | |
| | | Labrafil (an interestified hydrogenated palm | |
| Magnesium | 8 mg | | to make |
| stearate | 360 mg | oil) | 2 g. |

TABLE 1

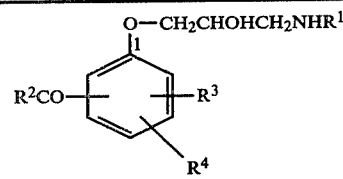

| Product (Code no.) | $R^1$ | $R^2$ | $R^4$ | $R^3$ | Re-crystal-lising solvent | Melting point °C. |
|---|---|---|---|---|---|---|
| 1 (CM 6718) | $CH(CH_3)_2$ | $2-C_2H_5$ | 4-Cl | $5-CH_3$ | hexane | 75 (a) |
| 2 (CM 6719) | $CH(CH_3)_2$ | $2-C_2H_5$ | 4-F | H | isopropyl ether | 114–5 (a) |
| 3 (CM 6721) | $CH(CH_3)_2$ | $2-C_2H_5$ | 4-Br | H | ethanol | 165 (b) |
| 4 (CM 6785) | $C(CH_3)_3$ | $2-C_2H_5$ | 4-Cl | H | methanol | 98–9 (a) |
| 5 (CM 6786) | $CH(CH_3)_2$ | $2-C_2H_5$ | 4-Cl | $6-CH_3$ | isopropyl ether | 62–4 (a) |
| 6 (CM 6804) | $C(CH_3)_3$ | $2-C_2H_5$ | 4-F | H | ethanol | 101–2 (a) |
| 7 (CM 6805) | $C(CH_3)_3$ | $2-C_3H_7$ | 4-F | H | ethanol | 87–8 (a) |
| 8 (CM 6826) | $CH(CH_3)_2$ | $2-C_3H_7$ | 4-F | H | ethanol | 95–6 (a) |
| 9 (CM 6827) | $C(CH_3)_3$ | $2-C_2H_5$ | 4-Cl | $6-CH_3$ | acetone | 158–9 (b) |
| 10 (CM 6831) | $CH(CH_3)_2$ | $2-C_2H_5$ | 2-Cl | H | isopropyl ether | 98 (a) |
| 11 (CM 6832) | $C(CH_3)_3$ | $2-C_2H_5$ | 5-Cl | H | ethanol | 124–5 (a) |
| 12 (CM 6833) | $CH(CH_3)_2$ | $2-C_2H_5$ | 5-Cl | H | ethanol | 132–3 (a) |
| 13 (CM 6834) | $CH(CH_3)_2$ | $2-C_2H_5$ | 4-Br | H | isopropyl ether | 84–5 (d) |
| 14 (CM 6836) | $C(CH_3)_3$ | $2-C_2H_5$ | 4-Br | H | isopropyl ether | 89–90 (a) |
| 15 (CM 6825) | $C(CH_3)_3$ | $2-CH_3$ | 4-Cl | H | ether (d) | 192–3 (c) | a: free base
b: acid fumarate
c: hydrochloride
d: ethyl ether

TABLE II

| Products | A β-blocking dose (intravenous) mg/kg | B Counteracting effect on isoprenaline % | | C Duration | D Rate of heart beat | E Peripheral-arterial pressure | F Ventricular pressure left | G Ventricular pressure right | H $\frac{de}{dt}p-1$ | I Cardiac output |
|---|---|---|---|---|---|---|---|---|---|---|
| | | FC | AP | | | | | | | |
| CM 6719 | 1 | 80 | 80 | 1 to 4 hrs ↓ | = | = | = | = | = |
| CM 6785 | 1 | 80 | 80 | 2 to 4 hrs ↓ | = | = | = | ↓ | = |
| CM 6804 | 1 | 90–100 | 90–100 | >3 hrs ↓ | ↓ or = | = | = | ↓ | = |
| CM 6805 | 0.5 to 1 | 90–100 | 90–100 | >3 hrs ↓ | = | = | = | = or ↓ | = or ↓ |
| CM 6826 | 2 | 80–85 | 85–100 | >3 hrs ↓ | = | = | = | ↓ | = |
| CM 6831 | 2 to 3 | 60–80 | 0–20 | 2 to 3 hrs ↓ | = | = | = | ↓ | = |
| CM 6833 | 0.2 | 65 | 0–100 | 2 hrs ↓ | = | = | = | ↓ | ↓ |

| Products | J Systolic volume | K Total peripheral resistance | L Maximum ventricular frequency | M Hisian electro-cardiogram AH ms  HV ms | N Fast gNa conductance | O Purkinje activating potential | P Ventricle activating potential |
|---|---|---|---|---|---|---|---|
| CM 6719 | = | = | ↓ | ↑   = | ↓ or = | = | ↑ |

TABLE II-continued

| | | | | | | | | |
|---|---|---|---|---|---|---|---|---|
| CM 6785 | ↓ or = | = | | ↓ | ↑ | = | ↓ | ↓ | = |
| CM 6804 | = | = | | ↓ | ↑ | = | ↓ | ↓ | ↓ |
| CM 6805 | = | = | = or ↓ | ↑ | = | ↓ | ↓ | ↑ |
| CM 6826 | = | = | | ↓ | ↑ | = | not tested | not tested | not tested |
| CM 6831 | = | = | | ↓ | ↑ | = | = | ↓ | = |
| CM 6833 | = | ↑ | | ↓ | ↑ | = | = | ↑ | = |

What I claim is:

1. A therapeutic composition useful in the treatment of pathological conditions associated with the over-production of catecholamines, including tachycardia, palpitations, extrasystoles and hypertension, which comprises, (a) as the active ingredient, a compound selected from the group consisting of 5-fluoro-2-(2-hydroxy-3-tertiary butyl-amino-propoxy)-butyrophenone, its optical isomers and non-toxic acid addition salts and (b) a physiologically acceptable excipient.

2. The therapeutic composition of claim 1 in an oral dosage form containing from 5 to 100 mg. of said active ingredient per dosage unit.

3. The therapeutic composition of claim 1 in a rectal dosage form containing from 5 to 100 mg. of said active ingredient per dosage unit.

4. The therapeutic composition of claim 1 in an injectible dosage form containing from 5 to 25 mg. of said active ingredient per dosage unit.

5. The therapeutic composition of claim 2, wherein the oral dosage form is a tablet.

6. The therapeutic composition of claim 3, wherein the rectal dosage form is a suppository.

* * * * *